(12) United States Patent
Stibrany et al.

(10) Patent No.: US 6,417,303 B1
(45) Date of Patent: Jul. 9, 2002

(54) SUBSTANTIALLY LINEAR COPOLYMERS

(75) Inventors: Robert T. Stibrany, Long Valley; Donald N. Schulz, Annandale; Smita Kacker, Clinton; Abhimanyu O. Patil, Westfield, all of NJ (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 0 days.

(21) Appl. No.: 09/435,178

(22) Filed: Nov. 5, 1999

Related U.S. Application Data

(63) Continuation-in-part of application No. 09/212,035, filed on Dec. 15, 1998, now Pat. No. 6,037,297, which is a continuation-in-part of application No. 09/991,160, filed on Dec. 16, 1997, now abandoned.

(51) Int. Cl.[7] .................................................. C08F 4/42
(52) U.S. Cl. ........................ 526/161; 526/164; 526/319; 526/324; 526/320; 526/329.7; 526/327
(58) Field of Search ................................ 526/161, 164, 526/319, 324, 320, 329.7, 327

(56) References Cited

U.S. PATENT DOCUMENTS

| | | | |
|---|---|---|---|
| 3,954,664 A | 5/1976 | Napier et al. | |
| 4,444,829 A * | 4/1984 | Bollen et al. | 428/220 |
| 4,471,068 A | 9/1984 | Haitko | |
| 4,477,589 A | 10/1984 | Van der Hulst | 502/169 |
| 4,740,644 A | 4/1988 | Eichhorn | 570/245 |
| 5,068,310 A | 11/1991 | Shaffer | |
| 5,266,665 A | 11/1993 | Hardiman | 526/117 |
| 5,278,272 A * | 1/1994 | Lai et al. | 526/348.5 |
| 5,316,994 A | 5/1994 | Kelsey | 502/117 |
| 5,369,073 A | 11/1994 | Sommazzi et al. | |
| 5,376,739 A * | 12/1994 | Pfleger et al. | 526/64 |
| 5,494,874 A | 2/1996 | Rosen | 502/526 |
| 5,556,823 A | 9/1996 | Sommazzi et al. | |
| 5,631,325 A * | 5/1997 | Latiolais et al. | 525/227 |
| 5,841,013 A | 11/1998 | Ho et al. | |

FOREIGN PATENT DOCUMENTS

| | | | |
|---|---|---|---|
| DE | 2060378 | 6/1972 | 502/165 |
| EP | 0560455 | 11/1993 | |
| EP | 0560456 | 11/1993 | |
| JP | 5439032 | 3/1979 | 502/165 |
| JP | 5594329 | 7/1980 | 502/165 |
| JP | 5622751 | 3/1981 | 502/167 |
| JP | 5738733 | 3/1982 | 502/165 |
| JP | 63159362 | 7/1988 | 502/167 |
| JP | 3275063 | 12/1991 | 502/165 |
| WO | 1996/23010 | 8/1996 | |

OTHER PUBLICATIONS

Todd R. Younkin, et al.; "Neutral, Single–Component Nickel (II) Polyolefin Catalysts That Tolerate Heteroatoms", Science, Jan. 21, 2000. vol. 287.

Encyclopedia of Polymer Science and Technology, vol. 6, Polar Copolymers, pp. 387, 409 & 414. (1967).

E.F. McCord, et al., Short–Chain Branching Structures in Ethylene Copolymers Prepared by High–Pressure Free–Radical POlymerization: An NMR Analysis, American Chemical Society, Macromolecules 1997, 30, 246–256.

Rajiv Bhalla, et al., Inorganic Chemistry, 1997, 36, pp. 2944–2949.

Prakash Chandra Vyas et al., Chemistry and Industry, Apr. 5, 1980.

Spencer Knapp et al., J. American Chemical Society, vol. 112, No. 9, 1990, pp. 3452–3464.

* cited by examiner

*Primary Examiner*—Bernard Lipman
*Assistant Examiner*—Ling-Siu Choi
(74) *Attorney, Agent, or Firm*—Joseph C. Wang

(57) ABSTRACT

The invention is directed towards substantially linear copolymers formed using a metal complex having the formula $LMX_1X_2$. L is a bidentate nitrogen-containing ligand with more than 2 nitrogens. M is copper, silver, or gold. $X_1$ and $X_2$ are independently selected from the group consisting of halogens, hydride, triflate, acetate, trifluoroacetate, perfluorotetraphenylborate, tetrafluoroborate, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, and any other moiety into which a monomer can insert. Such metal complexes have a tetrahedral or pseudo-tetrahedral structure and may be used with an activating cocatalyst. The invention is derived from polymers and copolymers using such catalyst compositions, especially copolymers having segments formed from olefinic monomers and monomers having at least one hydrocarbyl polar functional group.

15 Claims, No Drawings

SUBSTANTIALLY LINEAR COPOLYMERS

This application is a Continuation-In-Part of U.S. Ser. No. 09/212,035 filed Dec. 15, 1998 now U.S. Pat. No. 6,037,297 which is a Continuation-in-Part of U.S. Ser. No. 09/991,160 filed Dec. 16, 1997 abandoned.

FIELD OF THE INVENTION

The invention is directed towards tetrahedral and pseudo-tetrahedral late transition metal polymerization catalyst complexes and their use in forming homopolymers from olefins or polar monomers and copolymers from olefins and polar monomers.

BACKGROUND

Polymers and copolymers may be formed from olefinic monomers by using transition metal metallocene catalyst technology. This well-known technology uses catalysts containing early transition metal atoms such as Ti and Zr.

Even though polyolefins formed by such metallocene catalysts posses enhanced properties over polyolefins produced by conventional Ziegler-Natta catalysts, further improvements in properties such as wettability and adhesiveness may be possible. It is believed that including polar monomers in an olefinic polymer or copolymer would improve wettability and adhesiveness in those materials. Unfortunately, polar monomers tend to poison early transition metal catalysts.

Certain late transition metal complexes of palladium and nickel incorporate some polar monomers. However, such catalyst systems are costly. Also, the polymers so produced are highly branched (85–150 branches/1000 carbon atoms) and the functionalities are not in the chain but at the ends of branches. Consequently, they are limited to polar monomer contents ≦ about 15 mol%. Another disadvantage of these systems is that they incorporate only a limited number of polar monomers (e.g. alkyl acrylates and vinyl ketones). Methyl methacrylate and n-butyl vinyl ether are mildly inhibiting or inert.

Certain functional ethylene copolymers can also be made by free radical polymerization. In commercial practice, these materials also have significant short-chain and some long-chain branching (E. F. McCord, W. H. Shaw, Jr. and K A. Hutchinson, *Macromolecules*, 1997, 30, 246–256). Furthermore, some functional monomers (e.g. n-butyl vinyl ether) do not readily incorporate under free radical conditions (K. W. Doak, Encyclopedia of Polymer Science and Technology, 2nd Ed. H. F. Mark, Ed John Wiley and Sons, New York, 1986, Vol. 6, pp 387–429).

Consequently, there remains a need for a polymerization catalyst capable of forming olefinic polymers and copolymers and that are effective polymerization catalysts in the presence of polar monomers.

SUMMARY OF THE INVENTION

In one embodiment, the invention is a substantially linear copolymer represented by the formula:

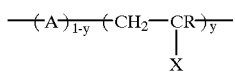

where A is a segment derived from an acyclic aliphatic olefin of 2 to about 20 carbon atoms;
R is H or $CH_3$;
X is $-OR^1$ or $-COOR^1$;
$R^1$ is an alkyl group of 1 to 24 carbon atoms; and Y is from about 0.02 to about 0.95

DETAILED DESCRIPTION OF THE INVENTION

One embodiment of the invention comprises comprises a substantially linear copolymers having the formula:

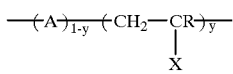

where A is a segment derived from an acyclic aliphatic olefin of 2 to about 20 carbon atoms; R is H or $CH_3$; x is $-OR^1$ or $-COOR^1$; $R^1$ is an alkyl group of 1 to 24 carbon atoms and y is from about 0.02 to about 0.95 and preferably y is from about 0.18 to about 0.85.

These copolymers have polar functional monomer segments,

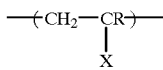

which are substantially in the chain rather than at ends of branches.

In the case where —A— is a polymer segment derived from ethylene, the branch content of which is below about 15 branches/1000 carbon atoms, for example from about 0.5 to less than 15 branches.

In another embodiment, the invention comprises a substantially linear copolymer having a polymer chain of the formula:

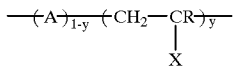

where A is a segment derived from an acyclic aliphatic olefin of 2 to about 20 carbon atoms. R is H or $CH_3$. X is $-OR^1$ or $-COOR^1$. $R^1$ is an alkyl group of 1 to about 24 carbon atoms and y is from 0.18 to 0.85.

In yet another embodiment, the invention comprises a substantially linear copolymer having a polymer chain comprising the formula:

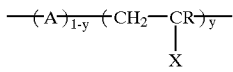

where A is a segment derived from ethylene. R is H or $CH_3$. X is $-OR^1$ or $-COOR^1$. $R^1$ is an alkyl group of 4 carbon atoms and y is from 0.18 to 0.85.

In another embodiment, the invention comprises a substantially linear copolymer having a polymer chain comprising the formula:

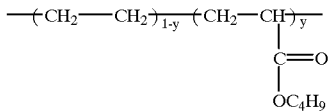

wherein y 0.02–0.95.

In another embodiment, the invention comprises a substantially linear copolymer having a polymer chain comprising the formula:

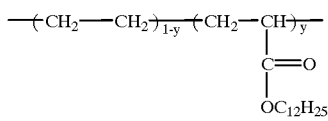

wherein y=0.02–0.95.

In another embodiment, the invention comprises a substantially linear copolymer having a polymer chain comprising the formula:

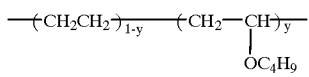

wherein y=0.02–0.95.

In another embodiment, the invention comprises a substantially linear copolymer having a polymer chain comprising the formula:

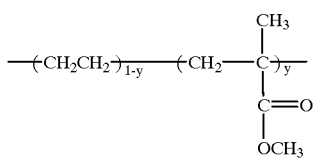

wherein y=0.02–0.95.

The catalyst used in the process to form this invention is a complex having the formula $LMX_1X_2$, wherein L is a nitrogen-containing bidentate ligand represented by the formula:

[AZA']

and

[AA'], wherein A and A' are independently selected from the group consisting of

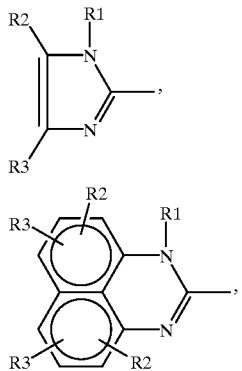

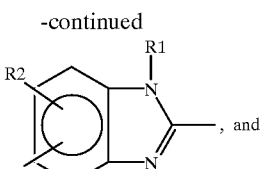

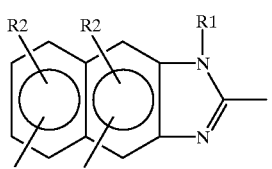

wherein R1 is independently selected from the group consisting of hydrogen, $C_1$ through $C_{12}$ straight chain or branched alkyl, $C_3$ through $C_{12}$ cycloalkyl, aryl, and trifluoroethane;

R2 and R3 are independently selected from the group consisting of hydrogen, $C_1$ through $C_{12}$ straight chain or branched alkyl, $C_3$ through $C_{12}$ cycloalkyl, $C_1$ through $C_{12}$ alkoxy, F, Cl, $SO_3$, $C_1$ through $C_{12}$ perfluoroalkyl, and $N(CH_3)_2$;

Z is selected from the group consisting of non-substituted $C_1$ through $C_{12}$ straight chain or branched alkyl, $C_3$ through $C_{12}$ cycloalkyl; methoxy; amino; halo; and $C_1$ through $C_{12}$ haloalkyl substituted straight chain or branched alkyl or cycloalkyl of up to 12 carbon atoms or $C_1$–$C_{40}$ aryl or alkylaryl groups.

$X_1$ and $X_2$ are independently selected from the group consisting halogens, hydride, triflate, acetate, trifluoroacetate, tris ([perfluorotetraphenyl) borate, and tetrafluoro borate, $C_1$ through $C_{12}$ straight chain or branched alkyl or alkoxy, $C_3$ through $C_{12}$ cycloalkyl or cycloalkoxy, and aryl or any other ligand with which a monomer can insert;

Accordingly, some of the ligands of the present invention have the structures:

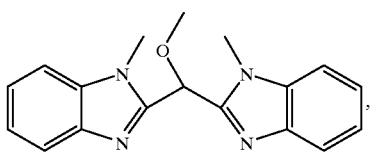

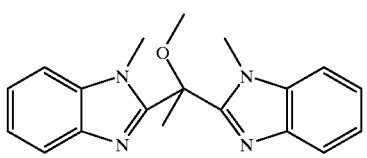

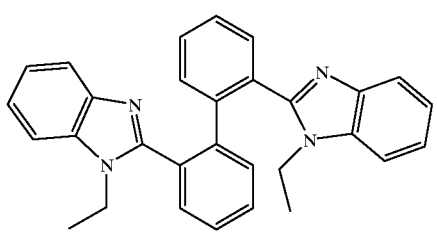

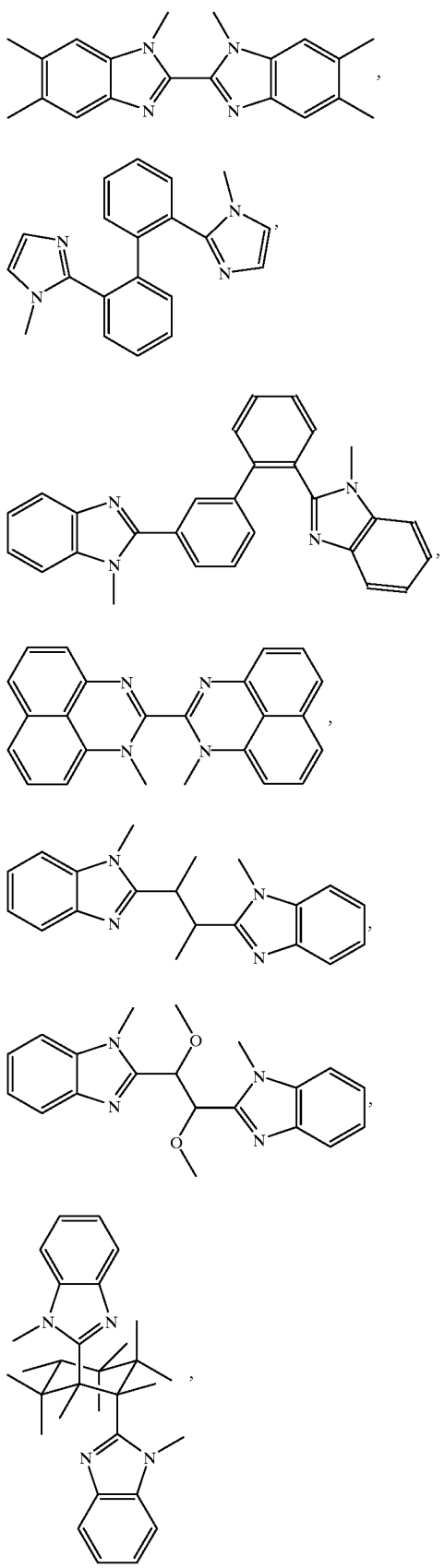

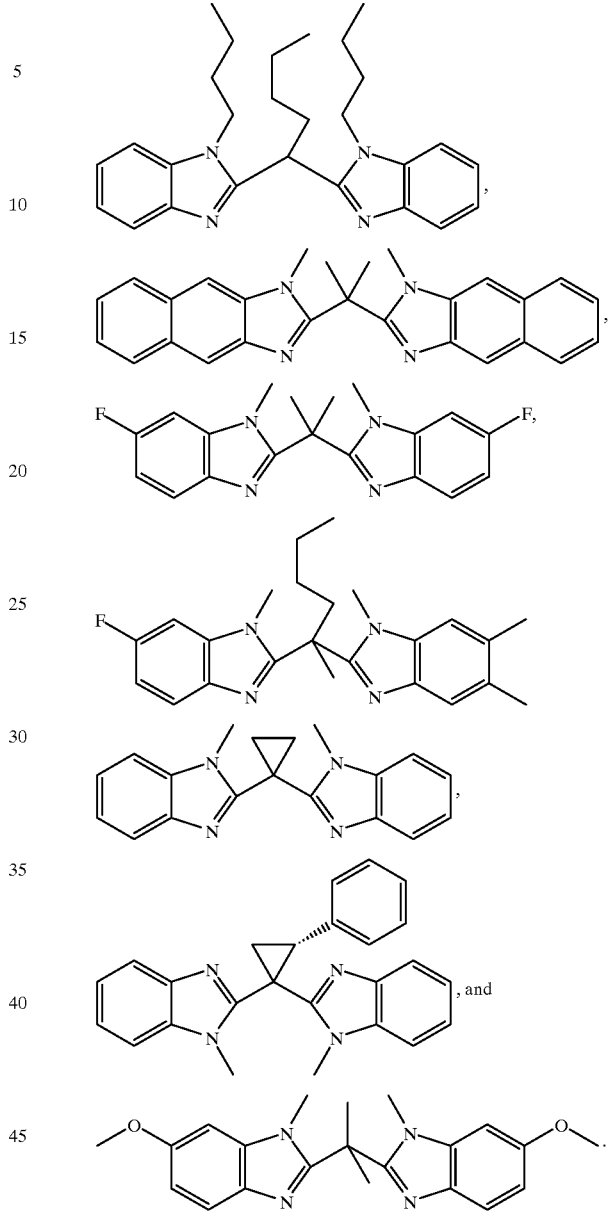

For compactness, some bonds are shown without termination; these bonds are terminated by methyl groups.

The metal M is selected from Cu, Ag, and Au. Among Cu, Ag, and Au, Cu is preferred; among $X_1$ and $X_2$, halogens are preferred.

Suitable non-halide $X_1$ and $X_2$ include triflate, tifluoroacetate, tris perfluorotetraphenyl borate, or tetrafluoro borate, hydride, alkyl groups or any other ligand into which a monomer can insert. Among the metal complexes of the present invention, those having the 1,1'bis(1-methylbenzimidazol-2yl)1" methoxyethane ligand or the 3,3'(1-ethylbenzimidazol-2yl) pentane ligand, or 2,2'bis[2-(1-alkylbenzimidazol-2yl)] biphenyl, where the alkyl group is from $C_1$–$C_{20}$, and $X_1$ =$X_2$=chloride are particularly preferred.

1,1'bis(1-methylbenzimidazol-2yl)1" methoxyethane ligands with copper as the metal and chlorine as $X_1$ and $X_2$ have the structure

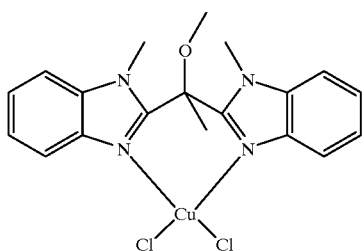

3,3'(1-ethylbenzimidazol-2yl) pentane ligands with copper as the metal and chlorine as $X_1$ and $X_2$ have the structure

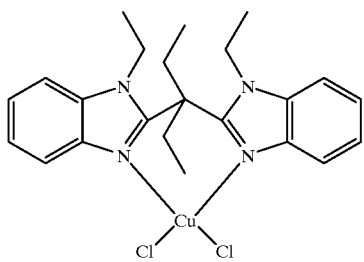

2,2'bis[2-(1-alkylbenzimidazol-2yl)]biphenyl ligands with copper as the metal and chlorine as $X_1$ and $X_2$, and $C_1$–$C_{20}$ as $R_1$, have the structure

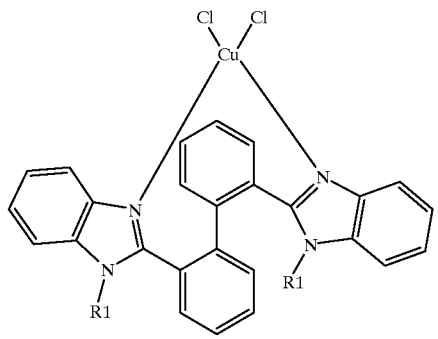

Advantageously, the catalysts used to form the present invention are not poisoned by compounds containing hydrocarbyl polar functional groups when used in the formation of polymers and copolymers synthesized all or in part from olefinic monomers. As such, the catalysts of the present invention are useful in preparing polymers and copolymers formed from olefinic monomers, such as polyethylene; polymers and copolymers formed from monomers containing hydrocarbyl polar functional groups such as poly(methyl methacrylate); and copolymers derived from olefins and monomers containing hydrocarbyl polar functional groups such as poly (ethylene-co-methyl methacrylate).

A process used to form the present invention employs a metal complex having the formula $LMX_1X_2$, (wherein L, M, $X_1$, and $X_2$ are as previously defined) in combination with an activating cocatalyst. Examples of such activating cocatalysts include aluminum compounds containing an Al—O bond such as the alkylalumoxanes such as methylalumoxane ("MAO") and isobutyl modified methylalumoxane "dry" MAO; aluminum alkyls; aluminum halides; alkylaluminum halides; Lewis acids other than any of the foregoing list; and mixtures of the foregoing can also be used in conjunction with alkylating agents, such as methyl magnesium chloride and methyl lithium. Examples of such Lewis acids are those compounds corresponding to the formula: $R''''_3B$, or $R_3''''Al$ wherein R"" independently each occurrence is selected from hydrogen, silyl, hydrocarbyl, halohydrocarbyl, alkoxide, aryloxide, amide or combinations thereof, said R"" having up to 30 nonhydrogen atoms.

It is to be appreciated by those skilled in the art, that the above formula for the preferred Lewis acids represents an empirical formula, and that many Lewis acids exist as dimers or higher oligomers in solution or in the solid state. Other Lewis acids which are useful in the catalyst compositions of this invention will be apparent to those skilled in the art.

Other examples of such cocatalysts include salts of group 13 element complexes. These and other examples of suitable cocatalysts and their use in organometallic polymerization are discussed in U. S. Pat. No. 5,198,401 and PCT patent documents PCT/US97/10418 and PCT/US96/09764, all incorporated by reference herein.

Preferred activating cocatalysts include trimethylaluminum, triisobutylaluminum, methylalumoxane, alkyl modified alumoxanes, "dry" aliumoxanes, chlorodiethyaluminum, dichloroethylaluminum, triethylboron, trimethylboron, triphenylboron and halogenated, especially fluorinated, triaryl boron and aluminum compounds, carboranes and halogenated carboranes.

Most highly preferred activating cocatalysts include triethylaluminum, methylalumoxane, and fluoro-substituted aryl boranes and borates such as tris(4-fluorophenyl)boron, tris(2,4-difluorophenylboron), tris(3,5-bis(trifluoromethylphenyl) boron, tris(pentafluorophenyl) boron, pentafluorophenyl-diphenyl boron, and bis (pentafluorophenyl) phenylboron and tetrakis (pentafluorophenyl) borate. Such fluoro-substituted arylboranes may be readily synthesized according to techniques such as those disclosed in Marks, et al., J. Am. Chem. Soc., 113, 3623–3625 (1991). Fluorinated tetraaryl borates or aluminates and perfluoro tetranapthyl borates or aluminates, are also well known in the art.

The catalyst can be utilized by forming the metal complex $LMX_1X_2$ and where required combining the activating cocatalyst with the same in a diluent. The preparation may be conducted in the presence of one or more addition polymerizable monomers, if desired. Preferably, the catalysts are prepared at a temperature within the range from −100° C. to 300° C., preferably 0° C. to 250° C., most preferably 0° C. to 100° C. Suitable solvents include liquid or supercritical gases such as $CO_2$, straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, halogenated hydrocarbons such as chlorobenzene, and dichlorobenzene perfluorinated $C_{4-10}$ alkanes and aromatic and alkyl-substituted aromatic compounds such as benzene, toluene and xylene. Suitable solvents also include liquid olefins which may act as monomers or comonomers including ethylene, propylene, butadiene, 1-hexene, 3-methyl-1-pentene, 4-methyl-1-pentene, 1-octene, 1-decene, and 4-vinycylohexane, (including all isomers alone or in mixtures). Other solvents include anisole, methylcbloride, methylene chloride, 2-pyrrolidone and N-methylpyrrolidone. Preferred solvents are aliphatic hydrocarbons and aromatic hydrocarbon, such as toluene.

It is believed that the cocatalyst interacts with the catalyst to create a polymerization-active, metal site in combination with a suitable non-coordinating anion. Such an anion is a poor nucleophile, has a large size (about 4 Angstroms or more), a negative charge that is delocalized over the framework of the anion, and is not a strong reducing or oxidizing agent [S. H.

Strauss, Chem. Rev. 93, 927 (1993)]. When the anion is functioning as a suitable non-coordinating anion in the catalyst system, the anion does not transfer an anionic substituent or fragment thereof to any cationic species formed as the result of the reaction.

The equivalent ratio of metal complex to activating cocatalyst (where employed) is preferably in a range from 1:0.5 to 1:$10^4$, more preferably from 1:0.75 to 1:$10^3$. In most polymerization reactions the equivalent ratio of catalyst:polymerizable compound employed is from $10^{-12}$: to $10^{-1}$:1, more preferably from $10^{-9}$:1 to $10^{-4}$:1.

The catalysts used to prepare the present invention have a tetrahedral or pseudo-tetrahedral structure. It is believed that this structure is present when the catalyst is in the form of an isolated solid compound and when the catalyst is used in the presence of activating cocatalysts of this invention under homopolymerization or copolymerization conditions.

Olefinic monomers useful in the forming homo and copolymers with the catalyst of the invention include, for example, ethylenically unsaturated monomers, nonconjugated dienes, and oligomers, and higher molecular weight, vinyl-terminated macromers. Examples include $C_{2-20}$ olefins, vinylcyclohexane, tetrafluoroethylene, and mixtures thereof. Preferred monomers include the $C_{2-10}$ α-olefins especially ethylene, propylene, isobutylene, 1-butene, 1-hexene, 4-methyl-1-pentene, and 1-octene or mixtures of the same.

Monomers having hydrocarbyl polar functional groups useful in forming homo and copolymers with the catalyst of the invention, are vinyl ether and $C_1$ to $C_{20}$ alkyl vinyl ethers such as n-butyl vinyl ether, acrylates, such as $C_1$ to $C_{24}$, or alkyl acrylates such as t-butyl acrylate, and lauryl acrylate, as well as methacrylates such as methyl methacrylate.

In general, the polymerization may be accomplished at conditions well known in the prior art for Ziegler-Natta or Kaminsky-Sinn type polymerization reactions, that is, temperatures from –100° C. to 250° C. preferably 0° C. to 250° C., and pressures from atmospheric to 2000 atmospheres (200 Mpa). Suitable polymerization conditions include those known to be useful for metallocene catalyst when activated by aluminum or boron-activated compounds. Suspension, solution, slurry, gas phase or other process condition may be employed if desired. The catalyst may be supported and such supported catalyst may be employed in the polymerizations of this invention. Preferred supports include alumina, silica, and polymeric supports.

The polymerization typically will be conducted in the presence of a solvent. Suitable solvents include those previously described as useful in the preparation of the catalyst. Indeed, the polymerization may be conducted in the same solvent used in preparing the catalyst. Optionally, of course, the catalyst may be separately prepared in one solvent and used in another.

The polymerization will be conducted for a time sufficient to form the polymer and the polymer is recovered by techniques well known in the art and illustrated in the examples hereinafter. Of course care must be exercised otherwise some of the functional groups may be partially hydrolyzed upon work-up.

The invention is further described in the following non-limiting examples.

EXAMPLES

I. CATALYST PREPARATION

Example 1

Preparation of 1,1'bis(1-hydrobenzimidazol-2yl)carbinol (HBBIOH)

A mixture of 8.0 g of (66.6 mmol) of hydroxypropanedioic acid and 14.41 g (133.3 mmol) of 1,2-phenylenediamine in 90 mL of 4 N hydrochloric acid was refluxed for 18 h. The reaction mixture was cooled and the pH was adjusted to about 8 with ammonium hydroxide to give a pale-green solid. The solid was collected by filtration and dried in a vacuum oven to give 8.85 g of 1,1'bis(1-hydrobenzimidazol-2yl)carbinol. Yield: (50.3%); mp 238° C. (sub1); $^1$H NMR (500 MHz, $d^6$ DMSO) δ 7.50 (m, 4H), 7.15 (m, 4H), 4.70 (s, 1H), 2.55 (s, 1H). In these examples, NMR resonances are identified as "m" for multiplet and "s" for singlet. IR absorptions are denoted s for strong, m for medium, and w for weak.

Example 2

Preparation of 1,1'bis(1-methylbenzimidazol-2yl)1" methoxyethane (MeBBIOMe)

A 1.0 g (3.8 mmol) quantity of HBBIOH was suspended in 50 ml of dry TBF. Under Ar, sodium hydride (80% dispersion in mineral oil, 0.68 g, 22.8 mmol) was added to the suspension and was stirred for 0.5 h. A 2.16 g (15.2 mmol) quantity of iodomethane was added dropwise and allowed to stir for 18 h. The reaction mixture was quenched with saturated aqueous sodium sulfate solution. THF was removed by rotory-evaporation. The oil was washed with water and separated with methylene chloride followed by chromatography. The 1,1'bis(1-methylbenzimidazol-2yl)1" methoxyethane was recrystallized from a mixture of 2-propanol and cyclohexane to give 0.23 g of solid. Yield 18.9%; mp 194–195° C.; EI-MS 320; $^1$H NMR (CDCl$_3$) δ 2.29 (s, 3H), 3.27 (s, 3H), 3.67 (s, 6H), 7.26–7.36 (m, 6H), 7.79–7.82 (m, 2H).

Example 3

Preparation of Cu(MeBBIOMe)Cl$_2$

A solution of ethanol and triethylorthoformate was prepared by refluxing 30 ml of 100% ethanol and 4 ml of triethylorthoformate. A 245 mg (1.82 mmol) quantity of CuCl$_2$ (99.999% Aldrich) was dissolved in the ethanol/triethylorthoformate solution to form a yellow-green solution. After the addition of 584 mg (1.82 mmol) of solid MeBBIOMe an intensely yellow colored crystalline precipitate formed. The complex, [1,1'bis(1-methylbenzimidazol-2yl)1" methoxyethane] copper(II) dichloride, Cu(MeBBIOMe)Cl$_2$, was collected by filtration and dried under vacuum. Measurements revealed a melting point (mp) 262–263° C. (decomposition). Elemental analysis calculations predicted relative concentrations of C, 50.19 wt %; H, 4.40 wt %; Cl, 15.61 wt %; and Cu, 14.00 Wt %. Laboratory measurements found C, 50.11 wt %; H, 4.48 wt %; Cl, 15.87 wt %; and Cu, 14.1 wt %; The X-ray crystallographic structure is shown in FIG. 1; bond angles are N3-Cu1-Cl2 101.7°, N1-Cu1-Cl1 104.6°, Cl2-Cu1-Cl1 105.9°, N3-Cu1-Cl1 126.30, N1-Cu1-Cl2 129.60. Accordingly, this compound has a pseudo-tetrahedral structure.

Example 4

Preparation of Cu(tributBBIM)Br$_2$

A 260 mg (1.16 mmol) quantity of CuBr$_2$ (99.99% Aldrich) was dissolved in 25 mL of ethanol to form an orange-brown solution. After the addition of 365 mg (0.88 mmol) of solid 1,1'bis(1-butylbenzimidazol-2yl)pentane, (tributBBIM), prepared by the methods of Examples 1 and 2, using malonic acid, 1,2-phenylene diamine and butyl iodide as the alkylating agent, a red-brown solution formed. Then 1 mL of triethylorthoformate was added to the solution and filtered. Upon standing the complex, [1,1'bis(1-butylbenzimidazol-2yl)pentane]copper(II) dibromide, Cu(tributBBIM)Br$_2$, formed as long thin red prisms. The crystals were collected by filtration and air dried, mp 215° C. (decomp.). The X-ray crystallographic structure is shown in FIG. 2; bond angles were measured to be Br1-Cu1-N11 130.6°, N1-Cu1-Br1 106.4°, N11-Cu1-Br2 99.10, Br1-Cu1-Br2 100.50, N1-Cu1-Br2 134.8°. Accordingly, this structure has a pseudo-tetrahedral structure.

Example 5

Preparation of (3,3'(1-ethylbenzimidazol-2yl)pentane] copper(II) dichloride, Cu(tetEtBBM)C$_{12}$ and ditifuoromethylsulfonate, Cu(teEtBBIM)(trif)$_2$ 3,3'(1-Ethylbenzimidazol-2yl) pentane copper (II) dichloride, Cu(tetEtBIM)Cl$_2$ was prepared by the Examples 1–3, using malonic acid and 1,2 phenylene diamine and ethyl iodide as the alkylating agent. A suspension of 65 mg of [3,3'(1-ethylbenzimidazol-2yl)pentane]copper(II) dichloride, Cu(tetEtBBIM)Cl$_2$, was prepared in a solution consisting of 35 ml of methylene chloride and 0.5 ml of triethylorthoformate. To the stirred suspension 67.5 mg of silver trifluoromethylsulfonate, Ag(trif), was added. After stirring about 15 minutes the solution was filtered. After slow evaporation, the filtrate afforded bright blue prisms of Cu(tetEtBIM)(trif)$_2$ which were collected by filtration. X-ray crystallographic data revealed a=9.8303 Å, b=10.3048 Å, c=16.1909 Å, $\alpha$=80.3697°, $\beta$=72.7137°, $\gamma$=71.4988°, Volume=1480.29 Å$^3$.

Example 6

Preparation of 2,2'bis[2-(1-ethylbenzimidazol-2yl]biphenyl] copper(II), Cu(diEtBBIL)Cl$_2$ A solution of ethanol and triethylorthoformate was prepared by combining 35 mL of 100% ethanol and 4 mL of triethylorthoformate. A 500 mg (2.93 mmol) quantity of CuCl$_2$·2H$_2$O (Aldrich) was dissolved to form a green solution. After the addition of 500 mg (1.13 mmol) of solid diEtBBIL, ±2,2'bis[2-(1-ethylbenzimidazol-2yl)]biphenyl, prepared by the method of Example 1 and 2, using 2,2'-diphenic acid, 1,2-phenylenediamine, and ethyl iodide as alkylating agent, the mixture was refluxed for 5 minutes. Upon cooling an organe-brown microcystalline solid was obtained. The solid was collected by filtration, washed with triethylorthoformate and pentane, then air dried to give 585 mg of orange-brown solid; mp 206–207° C. (decomp). The orange-brown solid was recrystallized from hot nitromethane to give the yellow crystalline complex, ±2,2'-bis[2-(1-ethylbenzimidazol-2yl)]biphenylcopper(II) dichloride, Cu(diEtBBIL)Cl$_2$, which was collected by filtration and dried under vacuum; mp 275° C. (soften) 285° C. (decomp.); Anal. Calcd. Cu, 11.01 Found Cu, 11.01; IR(KBr pellet, cm$^{-1}$)3439 br, 3069 w, 2962 w, 1668 s 2947 sh, 2926s, 2852 m, 1465 s, 1418 s, 776 sh, 761 sh, 746 s. X-ray crystallographic data: N1-Cu1-N3 111°; P2(1)2(1), Z=4, a=15.980 Å, c=20.538 Å, $\alpha$=90°, $\gamma$=90°, Volume=5387.36 Å$^3$; solution EPR (toluene/nitromethane) A$_{11}$=15 Gauss.

Example 7

Preparation of [±2,2'-bis[2-(1-octylbenzimidazol-2yl)]biphenyl]copper(II) dichloride, Cu(diOctBBIL)Cl$_2$ A 200 mg quantity of CuCl$_2$·2H$_2$O (Aldrich) was dissolved in 15 ml of ethanol to give a green solution. Then 100 mg of diOctBBIL, prepared by the method of Example 1 and 2, using 2,2'-diphenic acid, 1,2 phenylenediamine and 1-iodooctane as the alkylating agent, was added as an oil, followed by the addition of 1 ml of triethylorthoformate. The mixture was heated to reflux for 10 min., then allowed to cool. Upon standing the solution afforded bright-yellow thin plates of [±2,2'-bis[2-(1-octylbenzimidazol-2yl)]biphenyl] copper(II) dichloride. The crystalline solid was collected by filtration and washed with pentane. Yield 110 mg, MP 152–153° C., Elemental Analysis for Cu: calcd 8.52; found 8.45; X-ray crystallographic data: space group P-1, Z=2, a=12.152 Å, b=14.099 Å, c=23.253 Å, $\alpha$=90.18°, $\beta$=90.09°, $\gamma$=95.29°, Volume=3967.0 Å$^3$.

II. HOMOPOLYMERIZATION AND COPOLYMERIZATION

Reactions were conducted under argon using Schlenk and glovebox techniques. All solvents and monomers were purified by standard techniques, Perrin, D. D., Armarego, W. L F. *Purification of laboratory Chemicals*; Pergamon: New York, 1988. 30% MAO in toluene, available from Albemarle, Inc. (Baton Rouge, La.), was used as received. General procedure for polymer workup: First a sufficient amount of methanol is added in order to quench the polymerization reaction. Then the mixture is added to 5 to 10 times its volume of methanol containing 10 ppm of 2,6 Di-tertbutyl-4-methylphenol, (BHT), in order to precipitate the polymer. Then 10 ml of 2 N HCl is added to the mixture containing the polymer and is soaked for a sufficient time to remove the catalyst and cocatalyst from the polymer. The polymer is generally collected by filtration and dried under vacuum. "RT" means ambient or room temperature, i.e. a temperature from about 20° C. to 26°C.

Example 8

Polyethylene

A glass lined Parr reactor was loaded in an Ar glove box with 14.1 mg (0.024 mmol) of Cu (diEtBBIL)Cl$_2$ followed by 30 mL of toluene to give a pale yellow partially dissolved solution. Next 2.0 mL of 30% MAO was added to give a nearly colorless solution. The Parr was sealed and taken to a hood containing the controller for the Parr and pressurized with 270 psig ethylene and polymerized at 80° C. for ~24 hours. The reaction was cooled, vented and quenched with MeOH. The product was collected by filtration, washed with MeOH and dried at 70° C. for 2 hours. Yield=16.15 g of white polymer. Turnover Number (TON), moles substrate converted/moles catalyst=24,000. $^{13}$C NMR (TCE, Cr(AcAc)$_3$) $\delta$ 29.5(s, —CH$_2$—). There were no detectable resonances for branching elsewhere in the spectrum, using the method of Randall J. Macromol.Sci., Rev. Macromol. Chem. Phys. C29 (292) 1989. (Branch content<0.5 branches/1000 carbon atoms.) The $^1$H NMR (TCE) $\delta$ 1.3 (s, —CH$_2$—) $\delta$ 0.95 (m, CH$_3$ end groups) ($\delta$ 4.95–5.10 (m, olefin end groups). The ratio of CH$_3$ to olefin end groups was>3:1. Polymer M$_n$=4,900, Mw=13,900, by GPC (in TCB); Tm=139.1° C., $\Delta$H=209.8 J/g.

Example 9

Polyethylene Polymerization, Hexane Slurry Conditions

Polymerization was run using a hexane slurry prepared by suspending 3.72 mg (0.0082 mmol) of CuMeBBIOMe)Cl$_2$ in hexane followed by activation with 2.5 mL of 10% MAO (0.004 mol). The reactor was pressurized with 125 psig of ethylene and heated to 60° C. for 0.5 h to yield 2.4 g of solid polyethylene (TON=10,900). Polyethylene Mn=150700, MVVD=2.33 by GPC (in TCE, polyethylene standard). Polymer T$_m$=140° C.

Example 10
Polyethylene Polymerization, Moderate Pressure Conditions

A high-pressure HASTELLOY™ reactor was loaded in an Ar glovebox with a slurry prepared by suspending 35 mg (0.077 mmol) of Cu(MeBBIOMe)Cl$_2$ in 4.0 mL of toluene followed by activation with 1.0 ml of 30% MAO (0.005 mol). The reactor was pressurized with 5.6 g (0.20 mol) of ethylene and heated to 80.5° C., resulting in a pressure of 5170 psig. The pressure dropped to 4390 psig over a 2.75 h period indicating an uptake of ethylene. The polymerization mixture was cooled and quenched with methanol to give 1.1 g of solid polyethylene. (20% yield based on ethylene) Polyethylene Mn=145,400, MWD=2.55, Tm=139° C., $\Delta H_f$=122 J/g.

Example 11
Polymerization of Ethylene

The polymerization was run using a slurry prepared by suspending 12.8 mg (0.022 mmol) of Cu(diEtBBIL)Cl$_2$ in 30 mL of toluene and 10 mL of 1,2-dichlorobenzene followed by activation with 2.5 ml of 30% MAO to give a yellow suspension. The Parr reactor was pressurized with 500 psig of ethylene and heated to 80° C. and maintained at 80° C. for ½h during which the pressure dropped from 730 psi to 580 psig. The polymerization mixture was cooled and quenched with methanol to give 7.97 g of solid polyethylene upon workup (TON=12,700 moles$^{PE}$/moles catalyst).

Example 12
Polyethylene Polymerization, Toluene Slurry

The polymerization was run using a toluene slurry prepared by suspending 20.8 mg (0.029 mmol) of [3,3'(1-ethylbenzimidazol-2yl)pentane]copper(II) ditrifluoromethylsulfonate, Cu(tetEtBBMI)(trif)$_2$ in 30 mL of toluene followed by activation with 2.0 mL of 30% MAO (0.01 mol) to give a yellow suspension. The PARR™ reactor was pressurized with 300 psig of ethylene and heated to 90° C. and further pressurized to 750 psig and maintained at 90° C. for 20 h during which the pressure dropped to 740 psi. The polymerization mire was cooled and quenched with methanol to give 210 mg of solid polyethylene upon workup. Polyethylene Tm=137° C.

Example 13
Copolymerization of Ethylene and 1-hexene

A high-pressure HASTELLOY™ reactor was loaded in an Ar glovebox with a slurry prepared by suspending 30.1 mg (0.066 mmol) of Cu(MeBBIOMe)Cl$_2$ in 2.0 mL of toluene followed by activation with 1.0 mL of 30% MAO (0.005 mol). This was followed by the addition of 0.67 g of 1-hexene. The reactor was pressurized with 4.1 g of ethylene (0.146 mol) and heated to 80° C. resulting in a pressure of 850 psig. The pressure dropped to 690 psig over a 1.5 h period and the polymerization mixture was cooled and quenched with methanol to give 1.6 g of solid copolymer. (33.5% yield based on charge of monomers) Copolymer Mi=133,500, MWD=2.51, Tm=107, 123° C.

Example 14
Poly(t-butyl acrylate)

A 20.1 mg (0.044 mmol) quantity of Cu(MeBBIOMe)Cl$_2$ was added to a 100 mL round-bottomed flask in an Ar glovebox. A 10 mL quantity of toluene was added to the flask, followed by 0.11 g of 30 wt. % MAO (0.57 mmol) resulting in an yellow slurry. 7.45 g of t-butyl acrylate (freshly distilled from CaCl$_2$ and stabilized with 300 ppm of phenathiazine) was added to the slurry. The flask was covered with aluminum foil and the mixture was allowed to stir at room temperature for 18 hours in the dark. At the end of this time period, the reaction was quenched with 5 mL of methanol and then the polymer was precipitated out in 150 mL of acidic methanol (10%). The polymer was isolated by filtration and dried under vacuum at 40° C. for a day. Yield: 57%. Mn=470,000; Mw=851,000; MWD=1.8. $^{13}$C NMR (ppm, CDCl$_3$): 28.2 (s, —CH$_2$—CH(COOC(C$\underline{H}_3$)$_3$)—), 34.3–37.6 (m, —$\underline{C}$H$_2$—CH(COOC(CH$_3$)$_3$)—), 42–43.5 (m, —CH$_2$—$\underline{C}$H(COOC(CH$_3$)$_3$)—), 80.5 (m, —CH$_2$—CH (COO$\underline{C}$(CH$_3$)$_3$)—), 173.2–174.1 (m, —CH$_2$—CH ($\underline{C}$OOC(CH$_3$)$_3$)—), 38% rr, 46% mr, 16% mm (by integration of methine peak).

Example 15
Poly(methyl methacrylate)

19.6 mg of Cu(MeBBIOMe)Cl$_2$ was added to 5 mL of toluene in a 100 mL round-bottomed flask in an Ar glovebox. To another 5 mL quantity of toluene, 4.41 g of methyl methacrylate (stabilized with 400 ppm of phenathiazine) was added, followed by 0.15 g of 30 wt. % MAO (0.78 mmol). This pale yellow solution was added to the flask, which was sealed and covered with aluminum foil. The reaction mixture was stirred at room temperature for 16 hours in the dark. At the end of this time period, the green-yellow reaction mixture was quenched with methanol and then tie polymer was precipitated out in 150 mL of acidic methanol (10%). The polymer was isolated by filtration and dried under vacuum at 50° C. for a day. Yield: 51%. M$_n$=140,000; Mw=635,000; MWD=4.6. $^1$H NMR (ppm, CDCl$_3$): 0.86, 1.02, and 1.21 (s, —CH$_2$—C(C $\underline{H}_3$)(COOCH$_3$)—), 1.5–2.2 (broad m) and 1.91 (s, —C $\underline{H}_2$—C(CH$_3$)(COOCH$_3$)—), 3.63 (s, —CH$_2$—C(CH$_3$) (COOC$\underline{H}_3$)—), 76% rr, 18% mr, 6% mm (by integration of methyl peaks at 0.8 (rr), 1.0 (mr), 1.2 (mm) ppm).

Example 16
Poly n-butyl Vinyl Ether

In an Ar glovebox a yellow suspension was prepared by adding 1.0 ml of 30% MAO to 25 ml of toluene containing 10.2 mg (0.022 mmol) of Cu(MeBBIOMe)Cl$_2$. Then 5.0 mL n-butyl vinyl ether (44 mmol) was added to the suspension. The mixture was allowed to stir at RT for 20 h during which time the mixture became a viscous pale red-brown solution. The polymerization was quenched with methanol. Upon workup 2.07 g of amorphous poly n-butyl vinyl ether was obtained Yield: 53%, IR (film, KBr plate, cm$^{-1}$) 2956 (s), 2930 (s), 2871 (s), 1464 (m), 1457 (m), 1377 (m), 1039 (s). $^1$H NMR (CDCl$_3$) δ 0.95 (t, CH$_3$), 1.3–1.9 (m, CH$_2$), 3.3–4.7 (m, CH—o, —O—Ch$_2$); ratio δ 0.95–1.9/ δ 3.3–4.7=3H/9H. $^{13}$C NMR (CDCl$_3$) δ 13.5 (s, CH$_3$), 19.5 (s, CH$_2$O, 31.0 (s, CH$_2$) 39.0–41.0 (m, CH$_2$), 67.5 (m, —OCH), 73.5 (m, —OCH$_2$). GPC: Mn=6300, M$_2$=30,000.

Example 17
Ethylene/t-Butyl Acrylate Copolymer

A Parr reactor was loaded with 33.5 mg (0.0679 mmol) of Cu (tet EtBBIM)Cl$_2$ followed by 35 mL of toluene, then by 2.0 mL of 30% MAO (0.01 moles) in an argon dry box to give a yellow suspension. The 6.0 mL (5.37g) (54 mmol) of t-butyl acrylate was added to give a yellow-green suspension. The Parr was sealed and set up in a hood and pressurized with 750 psig of ethylene and polymerized at 90° C. for 24 hours. The reaction mixture was cooled and quenched with MeOH. Subsequently, the contents of the reactor were added to ca 150 mL of MeOH giving a white precipitate. A 10 mg quantity of BHT and 25 mL of HCl were added, and the mixture was allowed to soak to dissolve catalyst residues. The polymer was extracted from the water phase with CH$_2$Cl$_2$ and Et$_2$O. The solvents were removed by vacuum and the polymer was dried in a vacuum oven at 55° C. to give 2.96 g of pale-green solid. Catalyst turnovers (TON) (moles substrate converted per mole of catalyst) for t-butyl acrylate is 307, for ethylene is 151. $^1$HNMR (CDCl$_3$) δ 0.7–0.85 (m CH$_3$ end groups), δ 1.1–1.25 (m—CH$_2$—), δ 1.4 (s—O—C(CH$_3$)$_3$)), δ 2.05–2.25 (broad m,

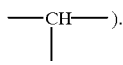

The presence of a multiplet rather than a triplet at 2.05–2.25 ppm, and the lack of a resonance at 1.6 ppm is consistent with in chain ester units rather than ester ended branches, such as —CH$_2$)$_n$CH$_2$COOC(CH$_3$)$_3$. Integration of the monomer units indicates a copolymer composition of ca 67% t-butyl acrylate units and 33% ethylene units. $^{13}$C NMR (δ, CDCl$_3$), δ 27 ppm (t, CH$_3$'s of the t-butyl group), δ67 (s,

of t-butyl group), δ 41.5–42.8 (m, —CH$_2$—), δ 43.8–44.8 (m, —CH$_2$—), δ 46.5 (s, —CH—). Branching analysis of CH$_3$ (at δ 19.8), Et (at δ 11.6), C$_3$-C$_6$ (at δ 14.1) by $^{13}$C NMR gave≦4.4 CH$_3$ branches/1000 C atoms, 7.7 CH$_3$CH$_2$ branches/1000 C atoms, and 5.1 propyl to hexyl branches/ 1000 carbon atoms. GPC (THF, polystyrene calibration, with DRI and UV detection at 215 nm) of a sample purified through a neutral alumina column to remove MAO and unreacted monomer: Mu=26,200, Mw=34,200. The presence of UV activity across the molecular weight distribution is an indication of copolymer formation. DSC (Tg=+4 and no Tm) also confirms copolymer rather than homopolymers.

Comparative Example 1

A copolymer was prepared following the procedure of Examples 134 of PCT WO96/23010. $^1$HNMR (CDCl$_3$): 2.2(t, —CH$_2$CO$_2$C(CH$_3$)$_3$, ester ended branches), 1.6 (m, CH$_2$CH$_2$CO$_2$C(CH$_3$)$_3$, ester ended branches), 1.45 (s, —C(CH$_3$)$_3$), 0.95–1.45, (m, CH, and other CH$_2$). 0.75–0.95 (m, CH$_3$, ends of hydrocarbon branches or ends of chains). This spectrum shows that the esters are primarily located at the ends of hydrocarbon branches; integration gave 6.7 mole % t-butyl acrylate. $^{13}$CNMR quantitative analysis, branching per 1000 CH$_2$: Total methyls (74.8); methyl (27.7), Ethyl (15.3), propyl 1.5), butyl (8.6), ≧amyl and end of chains (30.8), —CO$_2$C(CH$_3$)$_3$ ester (43.2). Ester branches —CH (CH$_2$)$_n$CO$_2$C(CH$_3$)$_3$ as a % of total ester: n≧5 (44.3), n=1, 2, 3, 4 (37.2), n=0 (18.5). GPC (THF, PMMA standard): Mn=6000 Mw=8310 Mw/Mn=1.39.

Example 18
Ethylene/MMA Copolymer

In an Ar glovebox, a Parr reactor was loaded with 26.1 mg (0.055 mmol) or orange Cu (BBIK) Cl$_2$, followed by 30 mL of toluene, and finally with 2.0 mL of 30% MAO (0.010 mol). Then 4.0 mL (3.74 g) (0.0374 mmol) of methyl methacrylate, containing 400 ppm of phenathiazine, was added. The Parr reactor was sealed and set up in a hood and pressurized with 750 psig of ethylene and polymerized at 90° C. for 19.5 hours. The reaction was quenched with MeOH. The polymer was collected by filtration to give 0.68 g of white polymer. Turnover Number (TON) (moles substrate converted for mole of catalyst) for MMA=109, for ethylene=50. IR (film, cm$^{-1}$l) 3441 w, 3001 s, 2951 s, 2943 sh,

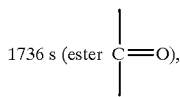

1456 (CH$_2$), 1246 s (C—O), 1149 s (C—O), 1000 sh, 991 s, 914 w, 844 m, 812 w, 756 m (CH$_2$). $^1$H NMR (CDCl$_3$) δ 0.61 (m, CH$_3$ end groups) δ 0.85–1.1 (m, CH$_3$). δ 1.45–2.45 (m, —CH$_2$—), δ 3.25–3.35 (s, —OCH$_3$). Integration of $^1$H NMR indicates a copolymer composition of 71.3% MMA and 28.7% ethylene. GPC (in TCB, polystyrene calibration): Mn=1,150, Mw=35,900; Tg of polymer-61.2° C. (first heat), no Tm; $^{13}$C NMR (CDCl$_3$), δ 18–22 (n, —CH$_2$—), δ 31–32, δ40–41 (m, —CH$_2$—), 45.5–46.5 (m,

δ 52.5 (s, —OCH$_3$), δ 55.8 (m, CH$_2$—). No backbone methine carbons were found by a DEPT (Distortionless Enhancement by Polarization Transfer) experiment, indicating no detectable backbone branch sites.

Example 19
Ethylene/n-Butyl Vinyl Ether Copolymer

A Parr reactor was loaded with 33.3 mg (0.0673 mmol) of Cu (tetEBBIM) Cl$_2$ and 30 mL of toluene, followed by the addition of 2.0 mL of 30% MAO (0.010 mol) to give a yellow suspension. A 5 mL quantity (44 mmol) of n-butyl vinyl ether was added with no immediate color change. The Parr reactor was sealed and taken to a hood containing the controllers for the reactor. The reactor was pressurized with 750 psig of ethylene and the mixture was reacted at 60° C. for 20 hours. The reaction was cooled, quenched and the product was isolated. The polymer was soaked in MeOH/ HCl to remove catalyst residues. The product was washed and dried to yield 0.420 g of viscous oil. TON (n-butyl vinyl ether)=61; TON (ethylene)=11.5. IR (film, KBr plate, cm$^{-1}$) 2958(s), 2931 (s)(CH$_2$), 2872(s), 1465(s), 1458(s), 1377(m), 1093(s), 1039(m), 979(w), 932(w), 913(w), 859(w), 802(m) 737(m) CH$_2$, $^{13}$C NMR (CDCl$_3$+CrAcAc)$_3$ δ 13.5 (s, CH$_3$), 19.5 (s, CH$_2$) 29.5–30.0 (m, —CH$_2$—), 31.0(s, CH$_2$) 39.0–41.5 (m, CH$_2$), 68.5(m, —CH—O), 73.5 (m, —OCH$_2$). The presence of the —CH—O resonance at 68.5 ppm indicates an in-chain copolymer. Integration of the NMR indicates a copolymer composition of 84.3% n-butyl vinyl ether, and 15.8% ethylene. The polymer Tg=97, −63° C. with no Tm is consistent with copolymer formation. GPC polystyrene calibration with DRI and UV detection at 215 nm), Mn=5390, Mw=23620, Mw/Mn=4.38. The presence of UV activity across the molecular weight-distribution confirms copolymer formation.

Example 20
Poly(lauryl acrylate)

In a nitrogen glovebox, a polymerization tube was loaded with 17.9 mg (FW 744.5, 2.4×10$^{-5}$ mole) of Cu(diOctBBIL) Cl$_2$ catalyst, followed by 20.25 mL of toluene, and finally with 0.8 mL of 10% MAO (0.00138 mole). Then 3.0 g (FW 240.39, 0.0125 mole) of inhibitor free lauryl acrylate was added. The mixture was allowed to stir at room temperature for 24 hours. The yield was 47%, upon workup. $^{13}$C NMR of the product showed characteristic polymer ester peak at 174.4 ppm as against to 166.1 peak for monomer ester. IR (film, cm$^{-4}$) 1736 (polymer ester carbonyl), 1464, 1396, 1377, 1258, 1167 and 721. GPC (solvent: THF, polystyrene calibration) of the product gave Mn 16100 and Mw 69100.

Example 21
Ethylene/Lauryl Acrylate Copolymer

In a nitrogen glove box, a Parr reactor was loaded with 15.0 mg (FW 744.5, 2.01×10$^{-5}$ mole) of Cu(diOctBBIL)Cl$_2$ catalyst, followed by 30 mL of toluene, and finally with 2.4 mL of 10% MAO (0.00414 mole). Then 2.0 g (FW 240.39, 0.00832 mole) of inhibitor free lauryl acrylate was added. The Parr reactor was sealed and set up in a hood and pressurized with 700 psig of ethylene and polymerized at 80° C. for 48 hours. The polymer was collected by filtration to give 1.3 g of product. Turnover number (TON) (moles of substrate converted for mole of catalyst) for LA=234, for ethylene=306. The $^{13}$C NMR of the product showed peaks due to both ethylene, as well as lauryl acrylate. Integration of the peak indicates a copolymer composition of 56.7 mole % ethylene, and 43.3 mole % lauryl acrylate. GPC (solvent: THF, polystyrene calibration) of the product gave Mw 7700.

What is claimed is:

1. A copolymer derived from late transition metal polymerization having a polymer chain comprising the formula:

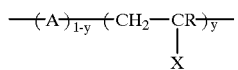

where A is a segment derived from an acyclic aliphatic olefin of 2 to about 20 carbon atoms;

R is H or CH$_3$;

X is —OR$^1$ or —COOR$^1$, wherein R$^1$ is an alkyl group of 1 to about 24 carbon atoms;

y is from about 0.02 to about 0.95; and the

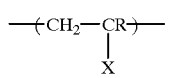

group is substantially in the polymer chain, wherein the copolymer is substantially linear.

2. The copolymer of claim 1 such that when A is a segment derived from an olefin of 2 carbon atoms, the segment A has a branch content of less than about 15 ethyl or higher branches/1000 carbon atoms.

3. A copolymer derived from late transition metal polymerization having a polymer chain comprising the formula:

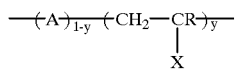

where A is a segment derived from an acyclic aliphatic olefin of 2 to about 20 carbon atoms;

R is H or CH$_3$;

X is —OR$^1$ or —COOR$^1$, wherein R$^1$ is an alkyl group of 1 to about 24 carbon atoms; and y is from 0.18 to 0.85, wherein the copolymer is substantially linear.

4. A copolymer derived from late transition metal polymerization having a polymer chain comprising the formula:

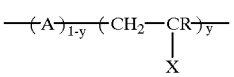

where A is a segment derived from ethylene;

R is H or CH$_3$;

X is —OR$^1$ or —COOR$^1$;

R$^1$ is an alkyl group of 4 carbon atoms; and y is from 0.18 to 0.85, wherein the copolymer is substantially linear.

5. A copolymer having a polymer chain comprising the formula:

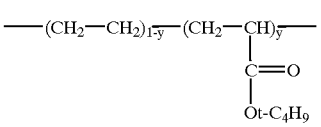

wherein y=0.02–0.95 and the copolymer is substantially linear.

6. A copolymer having a polymer chain comprising the formula:

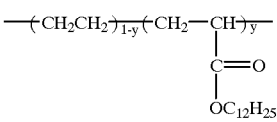

wherein y=0.02–0.95 and the copolymer is substantially linear.

7. A copolymer having a polymer chain comprising the formula:

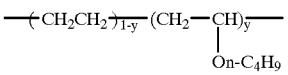

wherein y=0.02–0.95 and the copolymer is substantially linear.

8. A copolymer having a polymer chain comprising the formula:

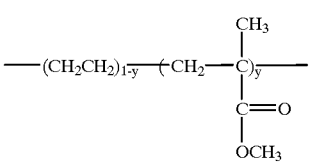

wherein y=0.02–0.95 and the copolymer is substantially linear.

9. The copolymer of claim 1 such that when A is a segment derived from an olefin of 2 carbon atoms, the segment A has a branch content of less than about 17 methyl to hexyl branches/1000 carbon atoms.

10. A copolymer derived from late transition metal polymerization having a polymer chain comprising the formula:

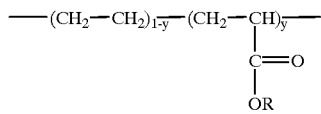

wherein y=0.02–0.95 and R is an alkyl group of from 1 to about 24 carbon atoms and further wherein the copolymer is substantially linear.

11. A copolymer derived from late transition metal polymerization having a polymer chain comprising the formula:

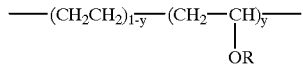

wherein y=0.02–0.95 and R is an alkyl group of from 1 to about 20 carbon atoms and further wherein the copolymer is substantially linear.

12. A copolymer derived from late transition metal polymerization having a polymer chain comprising the formula:

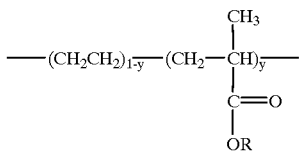

wherein y=0.02–0.95 and R is an alkyl group of from 1 to 24 carbon atoms and further wherein the copolymer is substantially linear.

13. A copolymer derived from late transition metal polymerization having from about 0.02 to about 0.95 of alkyl acrylate segments and the remaining portion being ethylene segments, wherein the copolymer is substantially linear.

14. A copolymer derived from late transition metal polymerization having from about 0.02 to about 0.95 of methyl methacrylate segments and the remaining portion being ethylene segments, wherein the copolymer is substantially linear.

15. A copolymer derived from late transition metal polymerization having from about 0.02 to about 0.95 of alkyl vinyl ether segments and the remaining portion being ethylene segments, wherein the copolymer is substantially linear.

* * * * *